US010399867B2

(12) United States Patent
Trigiani

(10) Patent No.: US 10,399,867 B2
(45) Date of Patent: Sep. 3, 2019

(54) ULTRASONIC ALGAE CONTROL

(71) Applicant: Antonio Trigiani, Bristol, TN (US)

(72) Inventor: Antonio Trigiani, Bristol, TN (US)

(*) Notice: Subject to any disclaimer, the term of this patent is extended or adjusted under 35 U.S.C. 154(b) by 54 days.

(21) Appl. No.: 15/586,261

(22) Filed: May 3, 2017

(65) Prior Publication Data
US 2017/0320756 A1 Nov. 9, 2017

Related U.S. Application Data

(60) Provisional application No. 62/348,265, filed on Jun. 10, 2016, provisional application No. 62/331,151, filed on May 3, 2016.

(51) Int. Cl.
C02F 1/36 (2006.01)
B06B 1/06 (2006.01)
(Continued)

(52) U.S. Cl.
CPC ............ C02F 1/36 (2013.01); A01M 21/04 (2013.01); A01M 21/046 (2013.01);
(Continued)

(58) Field of Classification Search
CPC ... A01M 21/04; A01M 21/046; B06B 1/0215; B06B 1/0644; C02F 1/008; C02F 1/36;
(Continued)

(56) References Cited

U.S. PATENT DOCUMENTS 5,126,616 A * 6/1992 Gorton ................. A61M 5/365
310/334
2008/0257830 A1 10/2008 Wu et al.
(Continued)

FOREIGN PATENT DOCUMENTS

CN 204 434 323 7/2015
NL 2000797 2/2009
(Continued)

OTHER PUBLICATIONS

International Search Report and Written Opinion of the International Searching Authority for International Application No. PCT/US2017/030937, dated Aug. 1, 2017, 20 Pages.

Primary Examiner — Patricck J Orme
(74) Attorney, Agent, or Firm — Knox Patents; Thomas A. Kulaga

(57) ABSTRACT

Apparatus for controlling algae and bio-organisms in bodies of fluids, such as water. The algae control system includes a power unit and a transducer unit that includes a sonic head that radiates in multiple directions. The power unit connects to various power sources, including a mains supply connection, a solar panel array, and/or a battery. The power unit is electrically connected to the transducer unit. The sonic head includes a driver and a transducer subassembly. The driver excites the transducer subassembly to emit ultrasonic waves at various frequencies in the water surrounding the sonic head. Emissions at a high density of frequencies are enabled by the transducers. The frequencies include the critical structural resonant frequency for each microorganism to be controlled. The power unit and driver each include a processor in communication with each other. The processors store and execute a program for a selected application configuration.

20 Claims, 8 Drawing Sheets

(51) Int. Cl.
  *A01M 21/04* (2006.01)
  *B06B 1/02* (2006.01)
  *C02F 1/00* (2006.01)
  *G01N 33/18* (2006.01)
  *C02F 103/00* (2006.01)

(52) U.S. Cl.
  CPC .......... *B06B 1/0215* (2013.01); *B06B 1/0644* (2013.01); *C02F 1/008* (2013.01); *G01N 33/1866* (2013.01); *C02F 2103/007* (2013.01); *C02F 2209/36* (2013.01); *C02F 2303/04* (2013.01)

(58) Field of Classification Search
  CPC ............ C02F 2103/007; C02F 2209/36; C02F 2303/04; G01N 33/1866
  See application file for complete search history.

(56) References Cited

U.S. PATENT DOCUMENTS

| | | |
|---|---|---|
| 2010/0126942 A1 | 5/2010 | Thottathil et al. |
| 2011/0000443 A1 | 1/2011 | Wu et al. |

FOREIGN PATENT DOCUMENTS

| | | | |
|---|---|---|---|
| NL | 2007561 | 4/2013 | |
| WO | WO2009020392 | 2/2009 | |
| WO | WO2013055207 | 4/2013 | |
| WO | WO-2013055207 A1 * | 4/2013 | ................ C02F 1/36 |

* cited by examiner

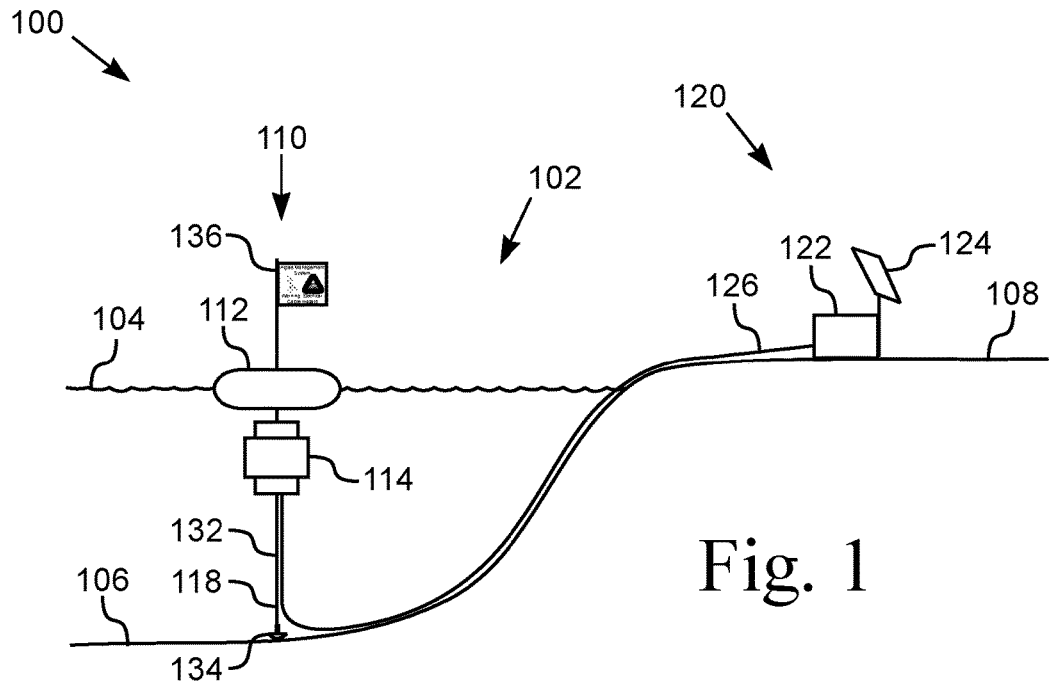
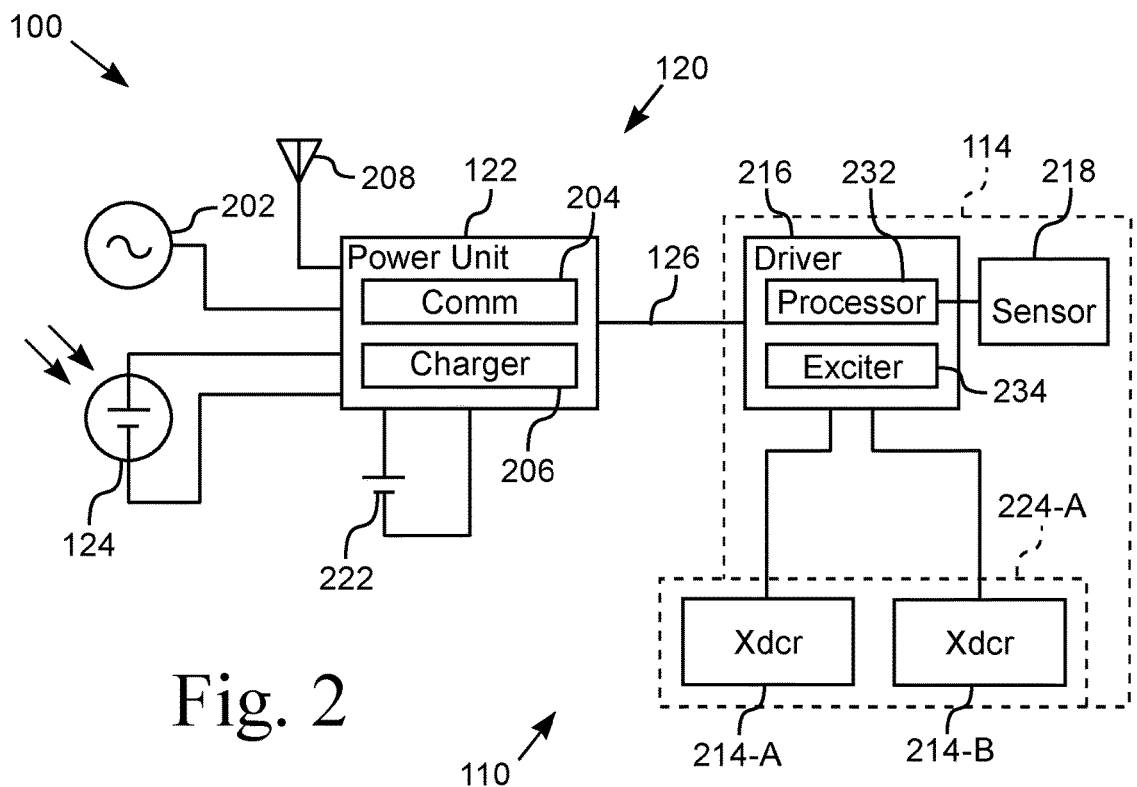

ULTRASONIC ALGAE CONTROL

STATEMENT REGARDING FEDERALLY SPONSORED RESEARCH OR DEVELOPMENT

Not Applicable

BACKGROUND

1. Field of Invention

This invention pertains to an apparatus for controlling algae and bio-organisms in bodies of water and for preventing layered bacterial formation (biofilm) where algae can attach on surfaces in that body of water. More particularly, this invention pertains to a power system and a corresponding ultrasonic transducer that radiates in multiple directions.

2. Description of the Related Art

Algae is a large, diverse group of photosynthetic organisms that often thrive in a water environment. When a body of water has an abundance of nutrients, algae thrives. Depending upon the type of algae, the algae growth may be beneficial or detrimental to the health of the body of water. For example, filamentous green algae and blue-green algae (cyanobacteria) are known for adversely affecting the health of a body of water when they grow in abundance.

Filamentous green algae is generally considered a nuisance that interferes with boater access, recreation, and aesthetics of the body of water. Green algae grows in mats, which can be physically removed from the water by raking or other means.

An excess of blue-green algae form surface blooms that are thick scums on the surface, typically near the shoreline. Some species of blue-green algae produce potent toxins that affect other aquatic and animal life. Blue-green algae are not edible, generally, and they produce an unpleasant odor when they decompose.

Control of undesirable algae, such as filamentous green algae and blue-green algae, can be accomplished by controlling the nutrient supply in the water. Without sufficient nutrients, the growth of algae will be limited. Unfortunately, controlling the nutrients in a body of water is often difficult because controlling the entry of nutrients into a body of water requires controlling the watershed. Both storm water drainage and agricultural drainage provide nutrients, and such sources are often difficult to manage.

Controlling undesirable algae by introducing chemicals into a body of water creates additional problems, particularly when the body of water contains other plant and animal life, such as commonly found in lakes, ponds, and streams. When the body of water is a swimming pool, hot tub, or spa, chemicals are often used to control or eliminate undesirable algae growth.

Another way to control undesirable algae growth is to reduce or remove the sunlight that the algae requires for photosynthesis. Floating plants, such a lilies and lotus, block the sunlight from penetrating the surface, thereby restricting the light reaching the algae. Other aquatic plants are grown in bodies of water to absorb the nutrients that the algae requires to flourish. For many bodies of waters, such as lakes and large ponds, adding plants is not practical.

Ultraviolet light is used to kill single cell algae by passing water by an ultraviolet light source. Ultraviolet light has no effect on filamentous algae. Generally, because of the power requirements, ultraviolet light is best suited for small volumes of water, such as aquariums, water gardens, and small ponds. In addition to the power for the ultraviolet light, power is needed for the pumping system.

BRIEF SUMMARY

According to one embodiment of the present invention, an algae control system is provided. The algae control system emits ultrasonic waves at targeted frequencies that are lethal to certain types of algae and microorganisms. The ultrasonic waves are emitted at frequencies that cause internal critical structural resonance within the organisms to be controlled, thereby killing the organisms. The algae control system includes a power supply unit and a transducer unit configured to be positioned in a body of fluid, such as water. In some embodiments, a cable connects the power supply unit to the transducer unit. In this way a stand-alone control system provides algae and other microorganism control in a body of water.

The power supply unit provides power and control signals to the transducer unit. In one embodiment, the power supply unit includes a processor and communications module, a solar panel, a charger, and a battery. In another embodiment the power unit includes a connection to an external mains supply. The processor allows for local control through various switches, a keyboard, and a display and for remote control through the communications module via a hardwired or wireless connection.

The transducer unit in one configuration includes a float that suspends a sonic head below the surface of a body of water where algae control is desired. In another configuration the transducer unit includes a buoyant portion supporting the sonic head, where the buoyant portion is anchored or secured to the bottom, thereby positioning the sonic head a distance above the bottom. In yet another configuration the transducer unit is secured to the bottom or another underwater surface with the sonic head supported between the surface and the bottom. The sonic head includes a driver and a transducer subassembly. The driver includes a processor, a power supply, and an exciter.

The transducer subassembly includes one or more ultrasonic transducers. The transducer assembly emits ultrasonic waves or vibrations in at least two directions separated by about a 90 degree angle. The ultrasonic waves or vibrations are emitted in a plane substantially parallel with the surface of the body of water when the sonic head is positioned in the body of water. In one embodiment, the transducer subassembly includes a pair of piezoelectric crystals, each sandwiched between two metal blocks. The two crystal-block assemblies are oriented 90 degrees apart in the horizontal plane when deployed, thereby providing substantially 360 degrees of ultrasonic coverage. In another embodiment, the transducer subassembly includes a piezoelectric crystal with one or more amplifier plates attached to the periphery of the crystal. The amplifier plates are separated by a small gap and are configured to radiate ultrasonic waves around the circumference of the crystal in a plane that is normal to the vertical axis of the sonic head when deployed.

The transducer unit emits sonic waves in a frequency band that targets green algae and diatom algae and in another frequency band that targets blue-green algae with gas vesicles. The control system driving the transducer subassembly considers factors including the frequency range and bandwidth, the time on/off at each discrete frequency, the step change from one frequency to the next, the power setting per frequency, and the size of the body of water in order to target a particular microorganism. These factors are programmable for specific applications, and, in one embodiment, the control system is remotely programmed. In this way the algae control system improves the control zone area per watt of energy consumed by configuration of the piezoelectric transducer and by voltage drop sensing and compensation in the device circuit to prevent loss of sound output levels. Also, the feature of installing programmed voltage set points for each ultrasonic frequency generated serves to maintain a consistent sound pressure output across the frequency bandwidths, which increases the overall range of control effectiveness.

In this way, the algae control system increases the frequency density in specific bandwidths where the microorganism control phenomenon of critical structural resonance occurs. The increased number of frequencies and frequency ranges, increases the number of microorganisms that can be controlled. Also, operating the algae control system within multiple frequency bandwidths enables targeting certain microorganisms, for example cyanobacteria (blue-green algae).

BRIEF DESCRIPTION OF THE SEVERAL VIEWS OF THE DRAWINGS

The above-mentioned features will become more clearly understood from the following detailed description read together with the drawings in which:

FIG. 1 is a symbolic view of one embodiment of the algae control system.

FIG. 2 is a block diagram of one embodiment of the algae control system.

DETAILED DESCRIPTION

Figure 3:
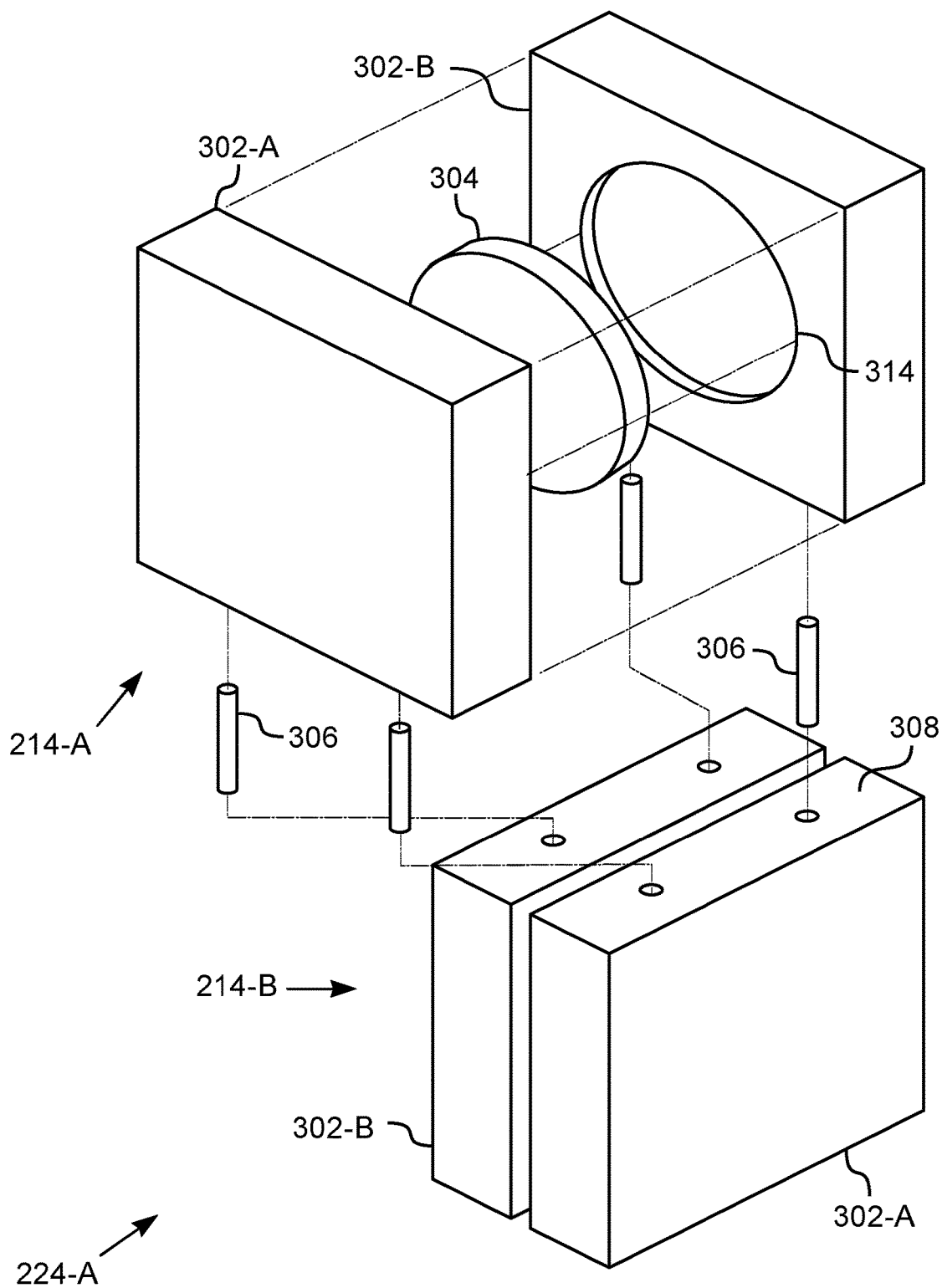
FIG. 3 is an exploded diagram showing one embodiment of a transducer subassembly.

Apparatus for an algae control system 100 is disclosed. Various components and elements, such as the first and second transducers 214-A, 214-B, have their particular embodiments and variations shown in the figures and described below with an alphabetic suffix. When referencing those components and elements generally, though, the suffix is omitted, such as when referencing the transducers 214. Positional references, such as horizontal and vertical, refer to the configuration of the algae control system 100 as it is deployed for use. For example, horizontal is considered parallel to the surface of the body of water 102.

FIG. 1 illustrates a symbolic view of one embodiment of the algae control system 100. The algae control system 100 includes a power supply unit 120 electrically connected to a transducer unit 110. The algae control system 110 is configured to be used with a body of water 102, such as a lake, a stream or river, a pond, a swimming pool, a spa or hot tub, or other body of water 102 in which algae overgrowth is to be controlled or eliminated.

The illustrated embodiment of the transducer unit 110 includes a floating device. The transducer unit 110 includes a float 112 with a flag 136, a sonic head 114, and an anchor system 118. The float 112 and anchor system 118 define the support structure for the sonic head 114. The support structure supports the sonic head 114 at a desired position in the body of water 102.

The transducer unit 110 is configured to float in a body of water 102, such as a pond, reservoir, or small lake. The float 112 is buoyant and rests on or near the surface 104 of the body of water 102. Suspended below the float 112 is the sonic head 114. The sonic head 114 is nominally 0.3 to 0.4 meters below the surface 104 of the water 102, although the depth of the sonic head 114 varies based on the requirements of the specific application configuration. For example, in a swimming pool or hot tub, the depth of the water 102 is such that the sonic head 114 provides adequate coverage when mounted on or near the bottom 106.

The float 112 is anchored to the bottom 106 of the body of water 102 by the anchor system 118. The anchor system 118 includes an anchor line 132 and an anchor 134 that engages the bottom 106. In one embodiment the sonic head 114 has an upper attachment point 402 for connecting to the float 112 and a lower attachment point 402 for connecting to the anchor system 118. In another embodiment the anchor system 118 is attached to the float 112 and the sonic head 114 attaches to the anchor line 132.

In another embodiment of the transducer unit 110, the sonic head 114 is buoyant and is secured to the bottom 106 with an anchor 134. The length of the anchor line 132 between the sonic head 114 and the anchor 134 establishes the depth of the sonic head 114 below the surface 104 of the body of water 102.

In yet another embodiment of the transducer unit 110, the transducer unit 110 is secured to a surface, such as a wall or bottom 106 of the body of water 102, with the sonic head 114 protruding from the surface into the body of water 102. Such an embodiment is suitable for a body of water 102 that is a small pond or a swimming pool where the volume of water to be treated by the transducer unit 110 is small enough that the position of the sonic head 114 is not critical to ensuring that the algae is controlled. For such a body of water 102, the transducer unit 110 protruding from the surface is unobtrusive while still being effective.

The illustrated power supply unit 120 is positioned on land 108 next to the body of water 102. The power supply unit 120 includes at least one solar panel 124 and a power unit 122, which provides power when a mains power supply is not available. In another embodiment, the power supply unit 120 is connected to a mains supply 202. A cable 126 connects the power supply unit 120 to the transducer unit 110. The cable 126 provides power and control signals to the transducer unit 110.

In another embodiment the power supply unit 120 includes a floating platform that is anchored in the body of water 102. For example, the power supply unit 120 is supported by dock floats, which are also the float 112 that forms part of the floating transducer unit 110. The power unit 122, battery pack 222, and solar panel 124 secured above the surface 104 of the body of water 102 by the float 112. In this way the power supply unit 120 and the floating transducer unit 110 are an integral unit. The integral combination of the power supply unit 120 and floating transducer unit 110 is able to be powered solely from the solar panel 124 (and associated battery 222) without reliance upon a mains power source 202. A further advantage of the integral combination is that the cable 126 has a short length, thereby minimizing power loss due to cable resistance. In yet another embodiment, the power supply unit 120 and the floating transducer unit 110 are an integral unit configured to be secured or attached to a structure in or defining the body of water 102, for example, the wall or floor of a swimming pool.

FIG. 2 illustrates a block diagram of one embodiment of the algae control system 100. The illustrated embodiment of the power supply unit 120 shows multiple power sources 124, 202, 222. The power sources include a mains supply 202, a solar panel 124, and a battery 222, all connected to the power unit 122. The mains supply 202 is an external power supply, such as a 120 Vac or 240 Vac mains connection. The solar panel 124 is an array of photovoltaic modules of solar cells. The solar panel 124 is connected to a battery charger 206 in the power unit 122 that charges a battery 222. The battery 222 is a pack of cells for storing the energy accumulated from the solar panel 124. The battery 222 is also charged by the mains supply 202, if there is one. For one embodiment of the power supply unit 120 having the mains supply 202, the solar panel 124, and the battery 222, the power supply unit 120 is operable as an uninterruptable power supply. In other embodiment the power supply unit 120 includes either a mains supply 202 or a solar panel 124 and a battery 222. In an embodiment of the power supply unit 120 having a battery 222, the power unit 122 includes a load monitor that shuts down the power unit 122 when the battery 222 nears depletion. In this way the battery 222 is protected from being totally discharged and thereby damaged.

The power unit 122 converts the power provided by the power sources 124, 202, 222 to a voltage level needed to power the sonic head 114. For example, the power unit 122 converts the 120 Vac mains power and/or the 24 Vdc battery power to the 40 Vdc operating voltage required by one embodiment of a sonic head 114. In various embodiments, one function of the power unit 120 includes selection of input power, such as between the mains supply 202, the battery 222, or the solar panel 124. Another function is controlling the power supplied to the transducer unit 110, such as by applying power according to a pre-defined schedule or by demand through local control or from a remote location. In one embodiment, the schedule includes time of day on/off periods thereby preventing certain aquatic life from feeding when the sonic head 114 is on or energized and allowing certain aquatic life to feed with the sonic head 114 off or de-energized. When the sonic head 114 is on or energized, the sonic head 114 is emitting ultrasonic waves. When the sonic head 114 is off or de-energized the sonic head 114 is not emitting ultrasonic waves.

The power unit 122 includes a communication module 204 that enables communication with a remote computer or other device. The communication module 204 has an antenna 208 for wireless communications. In another embodiment the communication module 204 includes a port allowing a local device to be connected to the module 204. An example of such a port is a universal serial bus (USB) connector. The communication module 204 is also connected to the cable 126, which includes data conductors. In one embodiment the communications module 204 includes a UART (universal asynchronous receiver/transmitter (UART) that communicates with the processor 232. New programming of the processor 232 is downloadable either from a remote location or by way of a local connection.

The power unit 122 is connected to the transducer unit 110 by a cable 126. The cable 126 carries power and the control signals required by the transducer unit 110. The cable 126, in one embodiment, include separate conductors 126-pwr, 126-comm for the power and the control signals. In another embodiment, the cable 126 includes power conductors 126-pwr that also carry the control signals.

The transducer unit 110 includes a sonic head 114 that has a driver 216, a sensor 218, and a transducer subassembly 224-A. The cable 126 supplies power to the driver 216 and also carries communication signals between the power unit 120 and the sonic head 114. In one embodiment, the communication signals are carried by conductors separate from the power carrying conductors in the cable 126. In another embodiment, the communication signals are carried by the power conductors, thereby eliminating the need for additional conductors in the cable 126.

In the illustrated embodiment, a sensor 218 is included with the sonic head 114 for sensing or measuring one or more characteristics associated with the algae control system 100. For example, in one embodiment, the sensor 218 samples the water 102 to determine the presence and/or concentrations of various microorganisms of interest. In one embodiment the sensor 218 includes a pump that draws in water 102 for a sample, tests the sample, determines the characteristics of the sample, and communicates the test results to the processor 232 in the driver 216. The processor 232 communicates with the communication module 204 in the power unit 122. The communication module 204 then communicates with a remote user, who determines the operating parameters of the sonic head 114 based on the results provided by the sensor 218. The remote user sends those operating parameters to the power unit 122, where the received data is then communicated to the processor 232 in the driver 216. The processor 232 then controls the exciter 234 to cause the transducers 214 to operate with the determined operating parameters.

The illustrated transducer subassembly 224-A includes at least a pair of transducers 214-A, 214-B that provide approximately 360 degree coverage horizontally. The transducers 214-A, 214-B operate at frequencies between 22 kHz and 220 kHz. Each one of the pair of transducers 214-A, 214-B is oriented to project waves 90 degrees, or normal, to the other, thereby providing substantially full, 360 degree coverage in a horizontal plane when deployed in the body of water 102.

The driver 216 is an electrical circuit connected to the transducers 214-A, 214-B. In one embodiment, the driver 116 operates the transducer 214-A, 214-B with a pre-defined duty cycle. In one such embodiment, each transducer 214-A, 214-B has a duty cycle with an on-cycle of 0.4 seconds and an off-cycle of 6 seconds. In one embodiment, the transducers 214-A, 214-B are operated simultaneously. In another embodiment, the transducers 214-A, 214-B are operated alternatingly, with one transducer 214-A emitting opposing waves for at least 180 degree coverage, with the other transducer 214-B, when energized, emitting opposing waves for at least 180 degree coverage that is offset from the first transducer 214-A. In this way full 360 degree coverage is provided by both transducers 214-A, 214-B.

The exciter 234 in the driver 216 causes the transducers 214 to be driven at various frequencies conducive to targeting specific microorganisms, such as Pythium fungi, green algae, and blue-green algae. In one embodiment the exciter 234 includes a PWM circuit that energizes the transducers 214 at a frequency and with a duty cycle controlled by the processor 232. In one embodiment the transducers 214-A, 214-B are operated with an on/off duty cycle that pulses the frequencies across a wide frequency range. For example, a first frequency is in the range between 24 and 58 kHz and a second frequency is in the range between 195 and 205 kHz.

The lower frequency range targets green algae and diatom algae. The upper frequency range targets blue-green algae with gas vesicles.

The processor, or microcontroller, 232 is programmed to drive the transducers 214-A, 214-B in a specified manner. In various embodiments, the programming of the processor 232 controls the following driver variables, or operating parameters: the frequency range and bandwidth, the time on/off at each discrete frequency, the step change from one frequency to the next, and the power setting per frequency. These variables are determined based on the microorganisms to be targeted, the size of the body of water, and the information, such temperature, pressure, light, and g-force, provided by any of various sensors 218. In one embodiment, the sensor 218 determines the presence and/or concentration of specific microorganisms. This information is sent from the sensor 218, to the processor 232, to the communications unit 204 to a remote location, where the driver variables are determined. After the driver variables are determined, they are sent to the communications module 204, through the cable 126 to the processor 232, which then operates the transducers 214-A, 214-B in accordance with the driver variables.

The frequency range and bandwidth is adjustable. For example, in one embodiment the frequency is adjustable between 10 kHz and 20 kHz in 10 Hz increments. The processor 232 is configured to cause the transducers 214-A, 214-B to emit at one or multiple frequencies. The processor 232 also controls the power or voltage setting for each frequency emitted. In this way the dB level is controlled. For example, higher frequencies requires more energy (higher voltages) in order to maintain a constant dB level of the emitted sonic wave. The size of the body of water 102 determines the power level required to effectively cover the body of water 102. The schedule of time on and off is determined to accommodate particular environments. For example, catfish may not feed when the transducers 214 are operating or energized. A feed schedule is determined to allow the catfish, or other aquatic life, to feed with the transducers 214 turned off or de-energized.

Other variables of concern include water temperature and pressure and light. The sensor 218, in one embodiment, measures the temperature of the water 102, the depth of the sonic head 114 and/or light around the system 100. In one embodiment, the processor 232 is programmed to adjust the driver variables based on the temperature, pressure, and light variables.

In another embodiment, the sensor 218 includes a humidity or moisture sensor responsive to the inside of the driver housing 416. Upon sensing a high humidity or moisture level, the processor 232 sends a water leak detected signal to the communications module 204, where a water leak detected alarm is given.

FIG. 3 illustrates an exploded diagram showing one embodiment of a transducer subassembly 224-A. The transducer subassembly 224-A includes a first transducer 214-A and a second transducer 214-B that are connected with isolators 306. The isolators 306 provide isolation of the vibrations from each transducer 214-A, 214-B from the other transducer 214-B, 214-A. The pins 306 fit into corresponding holes 308 in the blocks 302, thereby aligning and securing each pair of blocks 302-A, 302-B at right angles to each other while providing vibration isolation between the pairs of blocks 302-A, 302-B.

Each transducer 214 includes a pair of blocks 302 with an element 304 sandwiched therebetween. The element 304 is a piezoelectric crystal that vibrates when electric energy is applied to it. The blocks 302-A, 302-B are metal, such as aluminum or other metal that is conductive to vibratory frequencies originating from the element 304. The blocks 302-A, 302-B each have a recess 314 sized to receive the piezoelectric element 304. In one embodiment the piezoelectric element 304 is a crystal with electrodes on opposite sides. The electrodes extending from the piezoelectric element 304 are electrically connected to the driver 216. The blocks 302 have a mechanical connection with the sides of the element 304 and provide a large, flat surface for emitting ultrasonic waves. In one embodiment each element 304 is electrically bonded to each block 302-A, 302-B by a conductive adhesive on each face of the element 304. In this way the blocks 302 conduct the electrical energy from the driver 216 to the element 304, which then produces a vibratory frequency.

Figure 4:
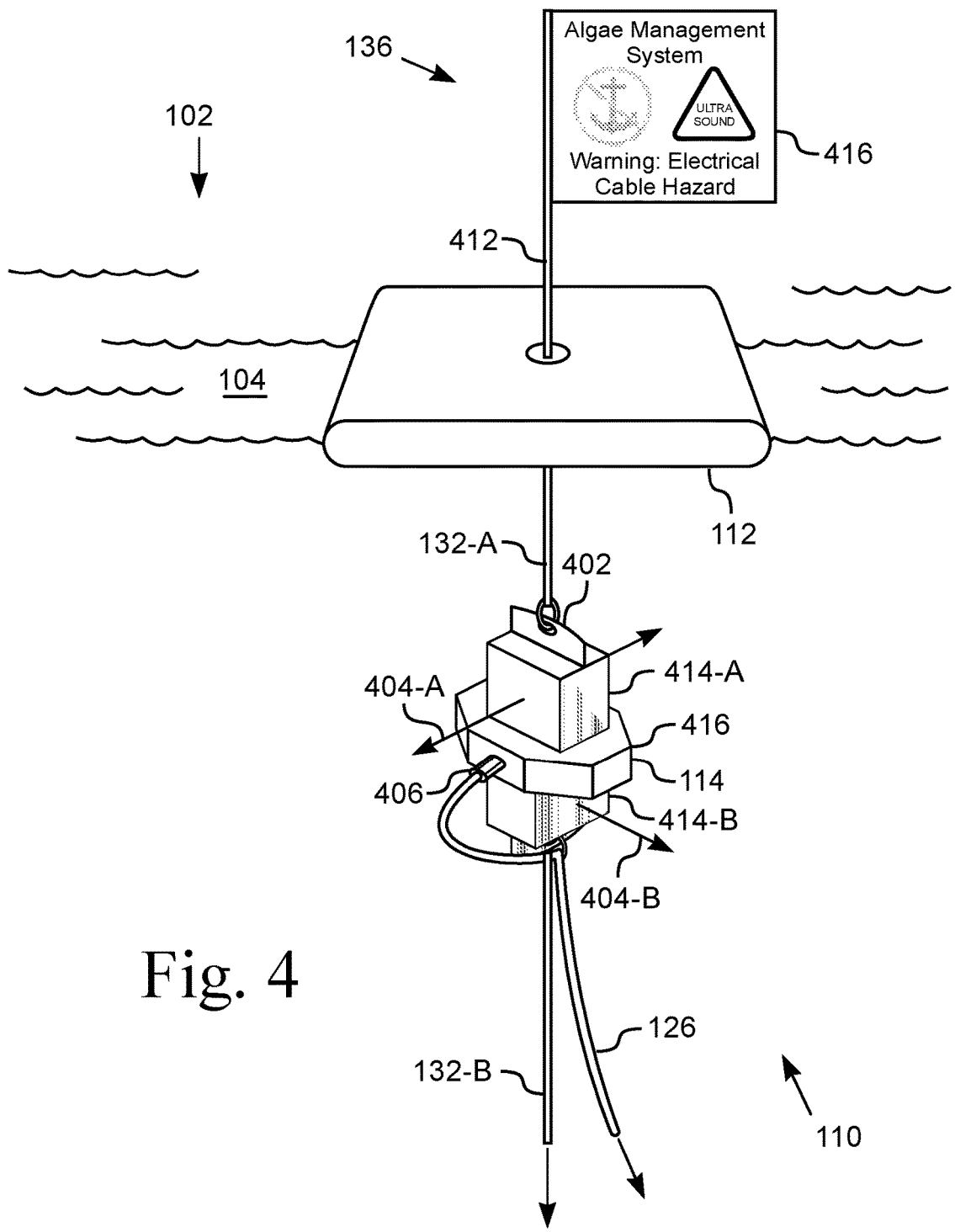
FIG. 4 is a partial side view of floating transducer unit in the water.

FIG. 4 illustrates a partial side view of a floating transducer unit 110. A float 112 has sufficient buoyancy to support the floating transducer unit 110 and a portion of the cable 126 with the float 112 at the surface 104 of the water 102. Extending above the float 112 is a flag 136. The flag 136 has a flag pole 412 and a banner 416 with markings. The flag 136 warns boaters and other waterborne users that there is an electrical device present in the vicinity.

In the illustrated embodiment, the sonic head 114 includes a pair of tabs 402 for attaching the anchor system 118. The upper anchor line 132-A attaches the float 112 to the top tab 402 of the sonic head 114. The upper anchor line 132-A has a length sufficient to hold the sonic head 114 at a desired depth below the surface 104. The lower anchor line 132-B attaches the bottom tab 402 of the sonic head 114 to the anchor 134 resting on the bottom 106. In another embodiment the float 112 is connected directly to the top tab 402 of the sonic head 114 without the use of an upper anchor line 132-A.

The sonic head 114 includes an upper transducer housing 414-A, a driver housing 416, and a lower transducer housing 414-B. A portion of the cable 126 runs along the lower anchor line 132-B, is secured to the lower tab 402 for strain relief, and has an end connector 406 mating with the driver housing 416.

The upper and lower transducer housings 414-A, 414-B are positioned such that the emitted sonic waves are at right angles to each other. The direction arrow 404-A extending from the upper housing 414-A shows the axis of the emitted sonic wave from the upper transducer 214-A. The direction arrow 404-B extending from the lower housing 414-B shows the axis of the emitted sonic wave from the lower transducer 214-B. The sonic waves are emitted and spread around the axes 404-A, 404-B. In this way the sonic head 114 provides sonic emissions radially 360 degrees for a volume below the surface 104 and centered at the sonic head 114.

Figure 5:
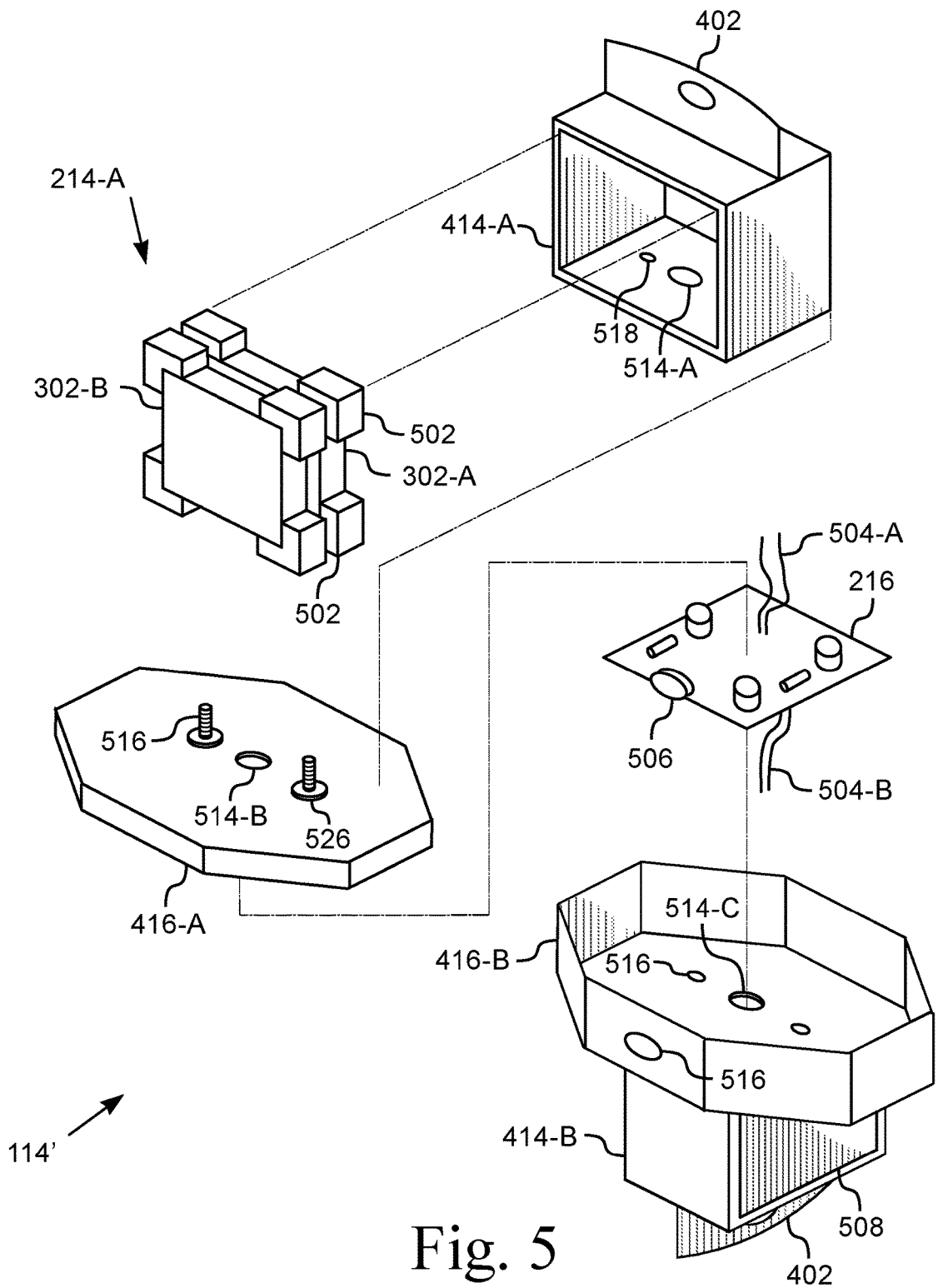
FIG. 5 is an exploded diagram of one embodiment of a sonic head.

FIG. 5 illustrates an exploded diagram showing another embodiment of a sonic head 114'. The upper transducer housing 414-A is shown separated from the upper half 416-A of the driver housing 416 and the transducer 214-A is shown separated from the upper housing 414-A.

The illustrated transducer 214-A has corner spacers 502 at each corner of each block 302-A, 302-B of the transducer 214-A. The upper housing 414-A has four surfaces. The transducer 214-A has a sliding fit inside the upper housing 414-A with the corner spacers 502 filling the space between the blocks 302 and the inside of the housing 414-A. The remainder of the space between the transducer 214-A and the housing 414-A is filled with a potting compound 508 or other waterproof filler such that the transducer 214-A is fully encapsulated inside the housing 414-A. In this way the transducer 214-A is protected from direct contact with the water 102 and the absence of air voids and pockets ensures the transmission of the sonic waves from the piezoelectric element 304 to the outside of the housing 214-A. The potting compound 508 fills the inside of the transducer housing 414-A flush with the edges of the open sides. The potting compound 508 has a density substantially the same as the water 102, thereby the ultrasonic waves emitted by the element 304 are conducted through the blocks 302, through the potting compound 508 and into the water 102 without being refracted or attenuated.

The driver housing 416 is illustrated in two parts: an upper driver housing 416-A and a lower driver housing 416-B that engages the upper housing 416-A. Inside the driver housing 416 is a cavity that receives the driver 216, which is illustrated as a circuit board with a connector 506 configured to receive the connector 406 at the end of the cable 126. The driver connector 506 mates with the cable connector 406 with a waterproof mechanical connection. The connector 506 on the driver 216 aligns with the opening 516 in the lower driver housing 416-B.

The housing as a first opening 514-A that is coincident with a corresponding opening 514-B in the upper driver housing 416-A. The upper driver housing 416-A includes openings through which fasteners 516 protrude. Between the outer surface of the upper driver housing 416-A and the lower, outer surface of the upper housing 414-A is a washer 526. Each fastener 516 engages one of a pair of threaded openings 518 in the upper transducer housing 414-A, thereby securing the upper transducer housing 414-A to the upper driver housing 416-A.

The driver 216 includes a pair of conductors 504-A that pass through the opening 514 in the upper driver housing 416-A and make electrical connection to the piezoelectric element 304 in the transducer 214-A. The driver 216 also includes a pair of conductors 504-B that pass through the opening 514-C in the lower driver housing 416-B and make electrical connection to the piezoelectric element 304 in the transducer 214-B. In one embodiment the conductors 504 make electrical contact with blocks 302, which are themselves electrically connected to the element 304. In one embodiment, the driver housing 416 is a waterproof enclosure. In another embodiment, the cavity in the driver housing 416 is filled with a potting compound or other waterproof filler.

Below the driver housing 416 is the lower transducer housing 416-B, which includes a lower transducer 214-B that is configured similarly to the upper transducer 214-A. The upper housing 416-A and upper transducer 214-A are oriented at a horizontal 90 degree angle relative to the lower housing 416-B and lower transducer 214-B. The axes of the emitted ultrasonic waves are normal or perpendicular to each other and oriented horizontally when the sonic head 114' is in the deployed position.

Figure 6:
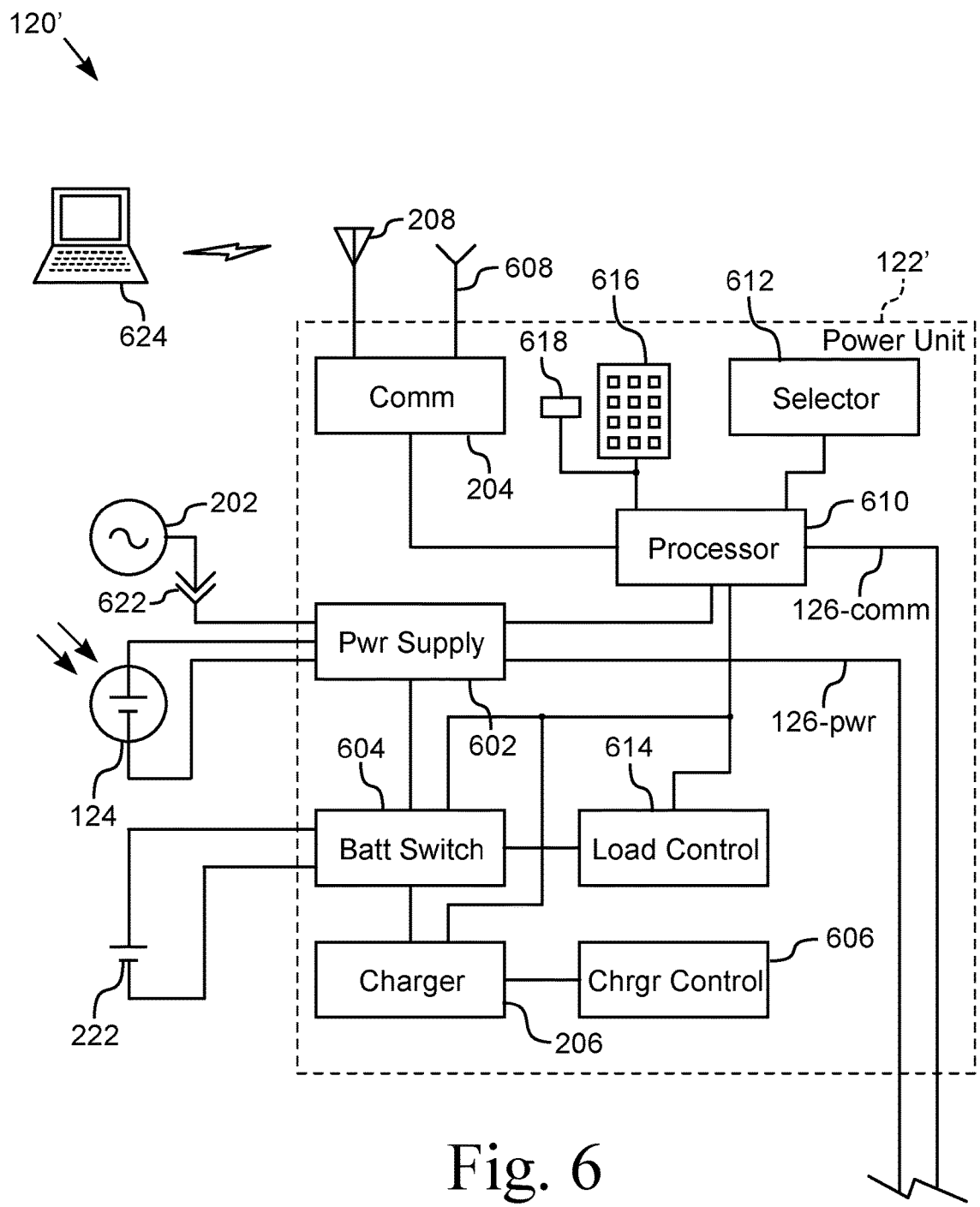
FIG. 6 is a block diagram of another embodiment of a power supply unit.

FIG. 6 illustrates a block diagram of one embodiment of a power supply unit 120'. The illustrated embodiment of the power supply unit 120' includes a connection 622 to a mains supply 202, a photovoltaic panel 124, a battery 222, and a power unit 122'. The power unit 122' includes a communications module 204 connected to a processor 610, a power supply 602 connected to a switch 604 and the processor 610, a load control 614 connected to the switch 604 and the processor 610, and a charger 206 connected to the switch 604 and a charger control 606.

The communications module 204 is connected to a wireless antenna 208 and an external device connector 608. A remote device 624, such as a laptop or other computing device, is in wireless communication with the antenna 208. In various embodiments the wireless communication is by way of Bluetooth, WiFi, MiFi, or other forms of wireless communication. In another embodiment the remote device 624 electrically plugs into the connector 608 for a direct electrical connection to the communications module 204.

The processor 610 is connected to input/output (I/O) devices such as a keyboard 616, a display unit 618, and an application configuration selector switch 612. In various embodiments, the keyboard 616 provides for direct alpha-numeric input to the processor 610, as well as menu selection. In various embodiments, the display unit 618 provides alpha-numeric output and status indication. For example, the display unit 618 works in conjunction with the keyboard 616 for entry of alpha-numeric data and menu selection. The display unit 618, in another embodiment, includes indicator lights providing status information. For example, for embodiments in which the processor 610 is connected to the charger 206, the display unit 618 shows the charge state and status of the battery 222 as a colored or blinking light or as an alpha-numeric display.

The processor 610 is connected to the other components in the power unit 122', such as the power supply 602, the battery switch 604, the battery charger 206, and the load control 614. In this way the processor 610 monitors and controls the power unit 122'. The processor 610 has an I/O link to the sonic head 114' though the cable 126-comm. In the illustrated embodiment, the cable 126 has multiple conductors with at least a pair of conductors 126-pwr dedicated to providing power and at least one other conductor 126-comm providing a communication connection with the sonic head 114'. In another embodiment, the power conductors 126-pwr also carry the control and communication signals instead of the signals being conducted along separate, isolated conductors 126-comm.

The application configuration selector switch 612 provides for manual selection of a set of pre-defined operating parameters for the sonic head 114'. An application configuration is a set of operating parameters for a specific set of conditions. For example, one application configuration defines the frequency range and bandwidth, the time on/off at each discrete frequency, the step change from one frequency to the next, and the power setting per frequency in order to target specific microorganisms in a specific type and size of body of water 102. The selection of an application configuration allows the algae control system 100 to operate in a pre-defined manner. In one embodiment, the selector switch 612 is a multi-gang DIP switch in which the digital number corresponding to a pre-defined configuration is selected by operating the individual switches.

The power supply 602 converts the voltage level of the input power sources to a transmission voltage level sent over cable 126-pwr. In one embodiment, the power supply 602 has an output of 40 Vdc that is sent to a power supply 702 in the sonic head 114'. The power supply 602, in various embodiments, has multiple inputs. The battery 222 is connected to a battery switch 604 that selectively connects the battery 222 to the power supply 602 as a power source or to the battery charger 206 for charging the battery 222. In another embodiment the battery 222 is connected directly to the battery charger 206, which functions to both charge the battery 222 and provide battery power to the power supply 602.

The battery charger 206 is powered by the power supply 602, which has a power source of either the power mains 202 or a solar panel 124. In one embodiment, a charger control

606 controls the battery charger 206. The charger control 606 is a switch that selects the battery type to be charged.

The power unit 122' in one embodiment includes a load control 614 that monitors the current state of charge of the battery 222 and isolates the battery 222 to prevent total discharge. For example, when the load control 614 determines that the battery 222 is within 10% of being fully discharged, the load control 614 operates the switch 604 to isolate the battery 222 from the power supply 602 and connect the battery 222 to the battery charger 206.

Figure 7:
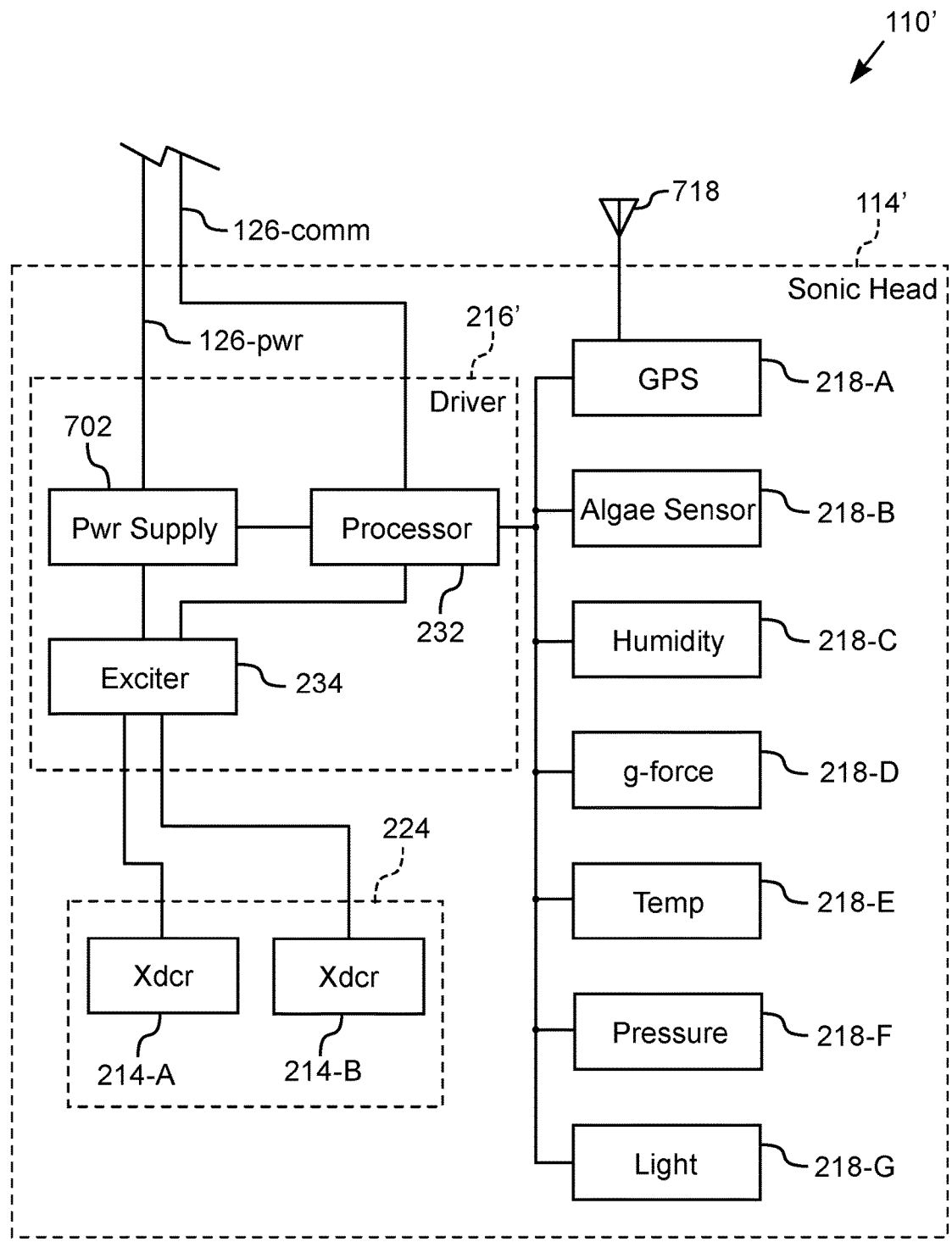
FIG. 7 is a block diagram of another embodiment of a transducer unit.

FIG. 7 illustrates a block diagram of one embodiment of a transducer unit 110'. The transducer unit 110' has a sonic head 114' that includes a driver 216', a transducer subassembly 224-A with a pair of transducers 214-A, 214-B, and various sensors 218-A to 218-G. In another embodiment, a transducer subassembly 224-A includes a single transducer 214-C.

The transducer unit 110' is electrically connected to the power supply unit 120' through the communications conductors 126-comm and the power conductors 126-pwr of the cable 126.

The driver 216' includes a power supply 702, a processor 232, and an exciter 234. The power supply 702 in the drive 216' is connected to the power supply 602 in the power unit 122' through the power conductors 126-pwr. The power supply 702 ensures that the proper power and voltage levels are maintained in the driver 216' regardless of the length of the cable 126 and any voltage drop in that cable 126.

The processor 232 in the driver 216' is connected to the processor 602 in the power unit 122' through the communication conductors 126-comm. In various embodiments, the two processors 610, 232 communicate via either a synchronous or an asynchronous serial connection. The processor 232 is also connected to the power supply 702, the exciter 234, and the various sensors 218-A to 218-G. The number and combination of sensors varies based on the particular configuration desired for the algae control system 100. In one embodiment, the sensors 218-A to 218-G have outputs that are processed directly by the driver processor 232 with resulting pertinent information communicated to the power unit processor 610. In another embodiment, the sensors 218-A to 218-G have outputs that are transmitted to the power unit processor 610, where the outputs are processed directly.

One sensor 218-A is a GPS unit with an antenna 718 mounted above the surface 104 of the water 102. In another embodiment, the entire GPS unit 218-A is located above the surface 104 of the water 102. The GPS unit 218-A is a Global Positioning System transceiver that provides location information to the processors 232, 610. With this information, the processors 232, 610 are able to determine if the transducer unit 110' has moved, such as by drifting or even by being stolen. Further, the processors 232, 610 are able to report on the current location of the transducer unit 110' for inventory control purposes.

Another sensor 218-B is an algae sensor that is responsive to the presence and/or concentration of various microorganisms in the surrounding water 102. With this information, the processors 232, 610 are able to determine the presence and/or concentration of the specific microorganisms desired to be targeted and adjust the operating parameters to target those detected microorganisms. For example, when green algae is detected, the processors 232, 610 control the sonic head 114 to emit ultrasonic waves with a frequency and/or duty cycle targeting the algae.

Another sensor 218-C is a humidity or moisture sensor that is responsive to the environment inside the driver housing 416. The humidity sensor 218-C has an output used by the processors 232, 610 to determine if a leak is present in the sonic head 114'. If a leak is detected by the humidity sensor 218-C, the power unit processor 610 communicates that information to a remote device 624 and/or indicates that information on the local display 618.

Another sensor 218-D is a g-force sensor that is responsive to movement of the sonic head 114'. In one embodiment the g-force sensor 218-D is an accelerometer with an output that varies based on the motions of the sensor 218-D in the sonic head 114'. For example, extreme wave motions in the body of water 102 indicate that the water is in motion, and that information is useful for determining the frequency and power output for the transducers 214. The output of the g-force sensor 218-D is used by the processors 232, 610 to determine an optimum application configuration or set of operating variables.

Another sensor 218-E is a temperature sensor responsive to the local water temperature. Another sensor 218-F is a pressure sensor responsive to the local water pressure, which indicates the depth of the sonic head 114'. The output of these sensors 218-E, 218-F are used by the processors 232, 610 to determine an optimum application configuration or set of operating variables.

Another sensor 218-G is a light sensor responsive to light intensity or luminescence in the water 102 surrounding the sonic head 114'. In one embodiment, the light sensor 218-G has an output used by the processors 232, 610 to control the power output of the transducers 214 and/or other operating parameters. For example, in some application configurations the power of the transducers 214 is increased during period of increased light, such as experienced during daytime hours. In one embodiment, the output of the solar panel 124 provides the same function as the light sensor 218-G.

As used herein, the processors 610, 232 should be broadly construed to mean any device that accepts inputs and provides outputs based on the inputs and the programming of the device. For example, each of the processors 610, 232 is a micro-controller, application specific integrated circuit (ASIC), an analog control device, or a computer or component thereof that executes software. In various embodiments, each of the processors 610, 232 is one of a specialized device or a computer for implementing the functions of the invention. Each of the processors 610, 232 includes input/output (I/O) units for communicating with external devices and a processing unit that varies the output based on one or more input values. Computer-based processors 610, 232 include a memory medium that stores software and data and a processing unit that executes the software. Those skilled in the art will recognize that the memory medium associated with the computer-based processors 610, 232 can be either internal or external to the processing unit of the processors 610, 232 without departing from the scope and spirit of the present invention.

The processors 610, 232 work independently and in tandem. In one embodiment, the processor 610 in the power unit 122' stores information on various pre-defined application configurations. The processor 610 also receives and stores new and revised application configurations from the remote device 624. When a specific application configuration is selected, such as locally from the selector switch 612 or the keypad 616, or remotely from the remote device 624, the processor 610 communicates with the driver processor 232, which stores the selected application configuration. The driver processor 232 executes its programming in accordance with the selected application configuration. The driver processor 232 provides status and sensor information to the power unit processor 610, which is programmed to respond and process such information.

Figure 8:
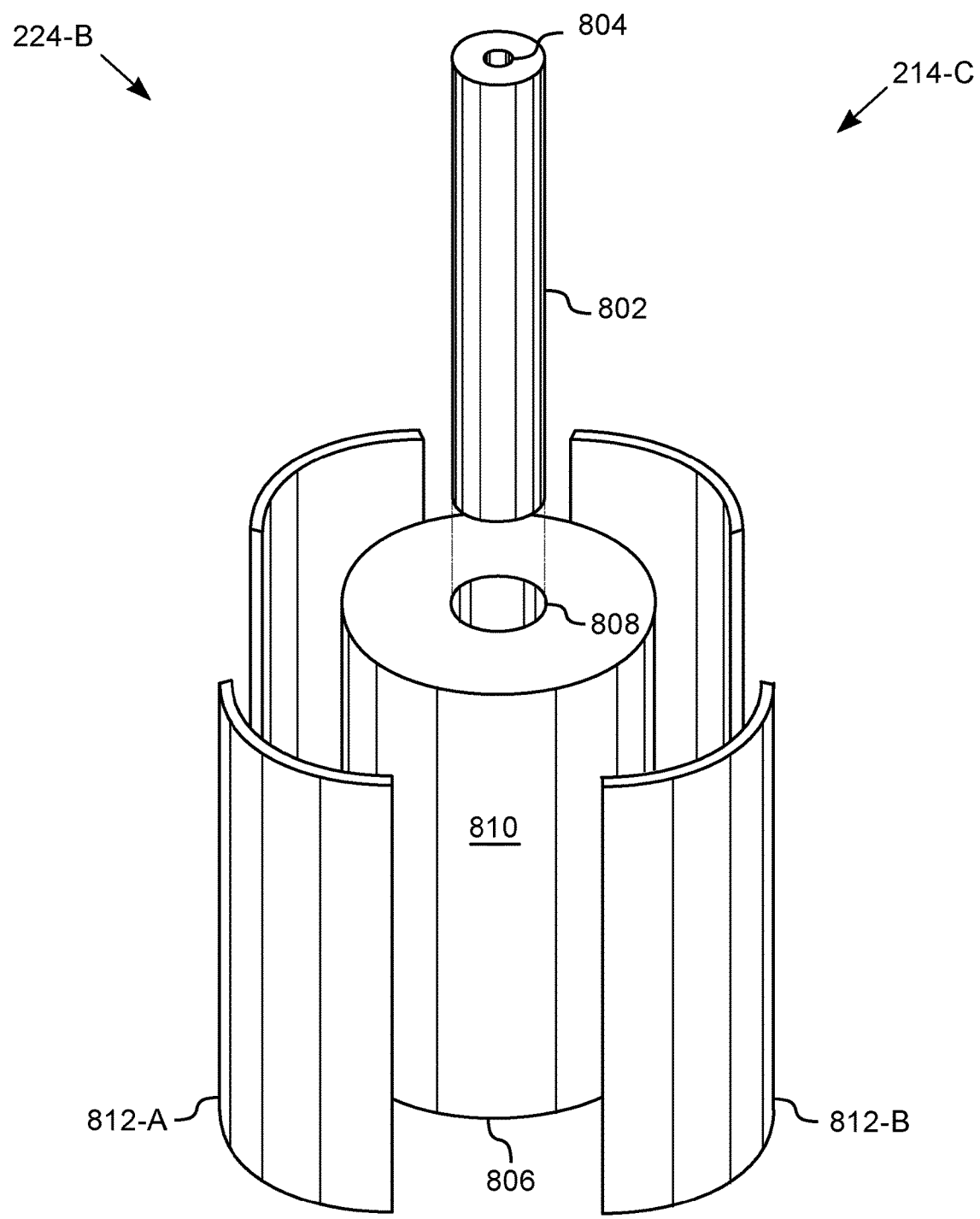
FIG. 8 is an exploded diagram showing another embodiment of a transducer subassembly.
Figure 9:
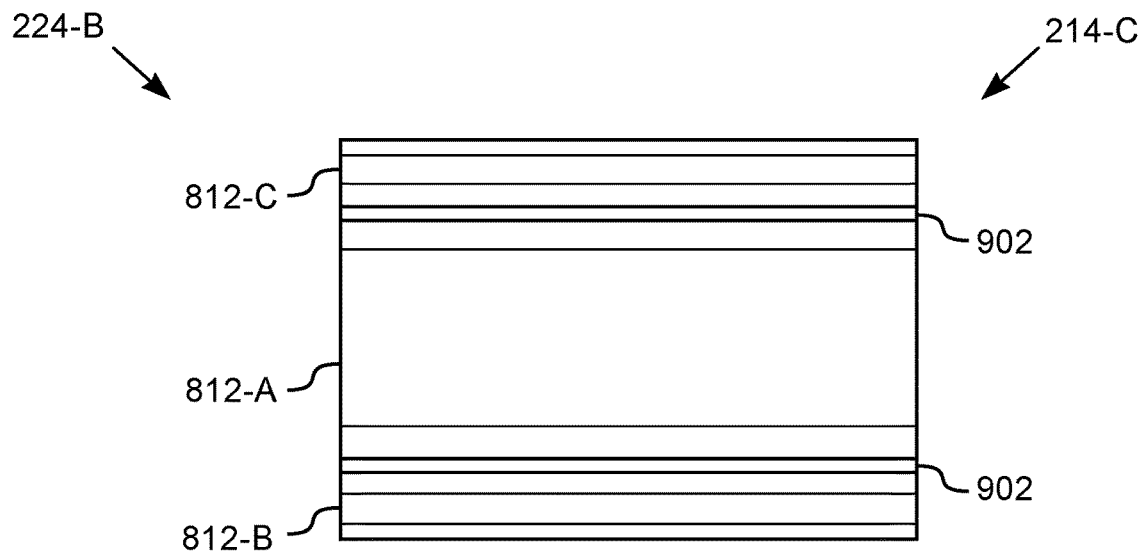
FIG. 9 is a side view of the transducer subassembly.
Figure 10:
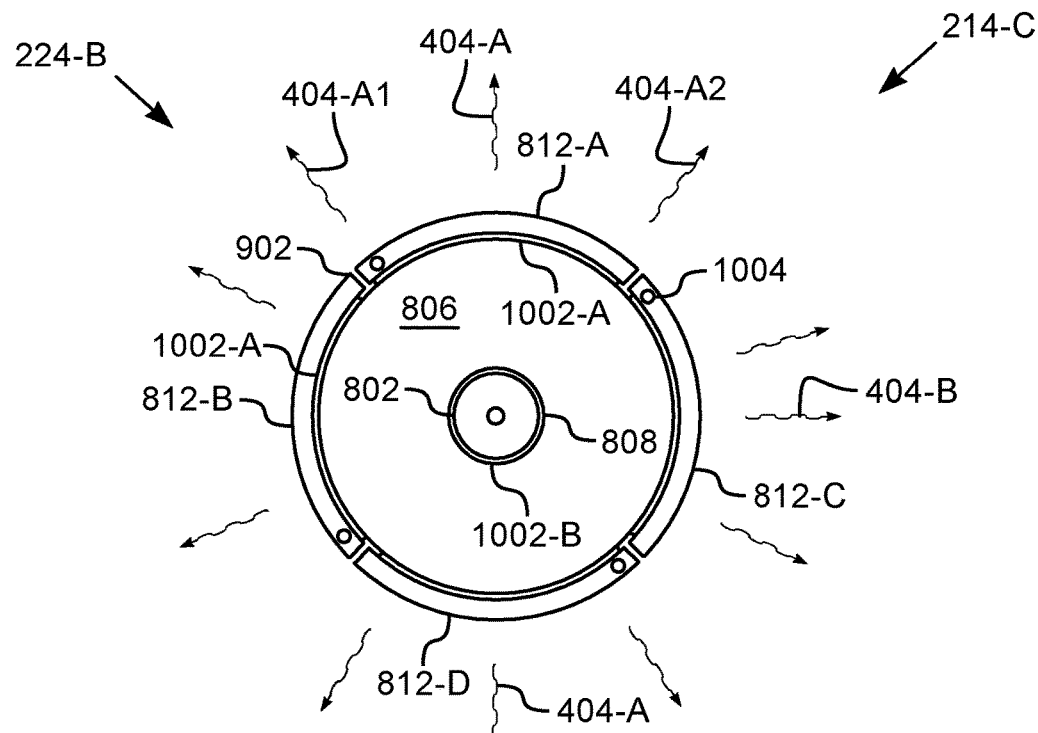
FIG. 10 is an end view of the transducer subassembly.

FIG. 8 illustrates an exploded diagram showing another embodiment of a transducer subassembly 224-B. FIG. 9 illustrates a side view of the transducer subassembly 224-B. FIG. 10 illustrates an end view of the transducer subassembly 224-B. The transducer subassembly 224-B includes a single transducer 214-C.

The various embodiments of the transducer subassembly 224 are configured to radiate ultrasonic waves 404 outward from the periphery of the transducer subassembly 224 in the horizontal plane when deployed such that the water 102 surrounding the transducer subassembly 224 is exposed to the ultrasonic waves 404. The direction arrows 404-A1, 404-A, 404-A2, 404-B represent the emitted ultrasonic waves emanating from transducer subassembly 224-B.

The transducer subassembly 224-B includes a piezoelectric element 806, a rod 802, and a set of radiators 812. The piezoelectric element 806 is cylindrical with a central bore 808. The outer, cylindrical surface 810 has an electrically conductive coating, such as silver. The inside surface of the central bore 808 likewise has an electrically conductive coating, such as silver. The rod 802 is electrically conductive and forms one-half of the electrical connection to the piezoelectric element 806. The end of the rod 802 includes a threaded opening 804 configured to receive a fastener connecting a conductor 504-A to the rod 802. The rod 802 is sized to fit inside the central bore 808 with enough clearance for an electrically conductive material or adhesive 1002-B to fit between the central bore 808 and the rod 802. In one embodiment, the electrically conductive material 1002-B is a conductive adhesive such as a silver epoxy.

The illustrated embodiment includes a set of four radiators 812-A, 812-B, 812-C, 812-D that have an inside surface that conforms to the outer, cylindrical surface of the piezoelectric element 806. The radiators 812-A, 812-B, 812-C, 812-D conduct the ultrasonic vibrations from the piezoelectric element 806 and radiate the vibrations as ultrasonic waves. In one embodiment, the radiators 812-A, 812-B, 812-C, 812-D are aluminum. The radiators 812-A, 812-B, 812-C, 812-D are electrically conductive and form one-half of the electrical connection to the piezoelectric element 806. The radiators 802 are attached to the electrically conductive coating 810 of the element 806 with an electrically conductive material or adhesive 1002-A. In one embodiment, the electrically conductive material 1002-A is a conductive adhesive such as a silver epoxy. One or more of the radiators 812 include a threaded opening 1004 configured to receive a fastener connecting a conductor 504-A to the radiator 812.

The radiators 812 are sized such that there is a gap 902 between adjacent ones of the radiators 812. The gap 902 permits the radiators 812-A, 812-B, 812-C, 812-D to vibrate independent of the adjacent radiators 812. In this way, for example, the ultrasonic waves 404 are emitted radially 404-A1, 404-A, 404-A2 from the plate 812-A. The gap 902 allows the other radiators 812-B, 812-C, 812-D to emit ultrasonic waves 404 similarly such that the full area in a plane perpendicular to the longitudinal axis of the piezoelectric element 806 is subject to ultrasonic waves 404.

In one embodiment, a single radiator 812 wraps around the piezoelectric element 802 and there is a single gap 902 that makes the radiator 812 discontinuous around the circumference of the piezoelectric element 802. In other embodiments, two or more radiators 802 surround the piezoelectric element 802.

The transducer subassembly 224-B is inserted in a transducer housing, which is then attached to the driver housing 416. In one embodiment, the transducer housing is can-shaped with a tab for connecting a line 132-A, 132-B, somewhat similar to the transducer housing 414-A illustrated in FIGS. 4 & 5. The transducer subassembly 224-B is encapsulated in a potting compound that is transparent to ultrasonic vibrations. In this way, the transducer subassembly 224-B is protected from the environment while not impeding the emission of ultrasonic waves.

In another embodiment, the transducer subassembly 224-B includes a transducer 806, which is a piezoelectric crystal, an electrode, or rod, 802, and at least one radiator 812. The electrode 806 fits into a bore 808 in the transducer, or piezoelectric element, 806. The at least one radiator 812 is attached to a peripheral surface of the transducer 806. The electrode 802 and at least one radiator 812 are electrically connected to the driver 216 and form an electrical circuit through the transducer 806.

The algae control system 100 includes various functions. The function of providing substantially 360 degree coverage in a plane parallel with the surface 104 of the body of water 102 is implemented, in one embodiment, by the pair of transducers 214, each oriented at 90 degrees with the other. In another embodiment, the function of providing substantially 360 degree coverage in a plane parallel with the surface 104 of the body of water 102 is implemented by a piezoelectric element 806 having a set of radiators 812 attached to an outer surface of the element 806 such that the radiators 812 emit ultrasonic waves with 360 degree coverage. Additionally, the emitted wave fans out vertically as the wave travels away from the transducers 214.

The function of controlling multiple types of microorganisms, is implemented, in one embodiment, by the transducers 214 emitting sonic waves at the critical structural resonant frequencies coincident with the microorganism to be controlled by internal damage. In one such embodiment, the function of controlling both green algae and diatom algae, along with blue-green algae, is implemented by the sonic head 114 emitting sonic waves at a first frequency range between 24 and 58 kHz and at a second frequency range between 195 and 205 kHz.

From the foregoing description, it will be recognized by those skilled in the art that a transducer unit 110 for controlling algae in bodies of water 102 has been provided. The transducer unit 110 includes a sonic head 114. In one embodiment, the sonic head 114 includes a pair of ultrasonic transducers 214-A, 214-B oriented to emit sonic waves at right angles to each other. In another embodiment, the sonic head 114 includes a transducer subassembly 224-B having a single transducer 214-C with a set of radiators 812.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for controlling microorganisms in a body of water, said apparatus comprising:
   a transducer assembly configured to emit sonic waves along a first axis, said transducer assembly configured to emit sonic waves along a second axis, said second axis at right angles to said first axis;

said transducer assembly including a first transducer and a second transducer, said first transducer having a first piezoelectric element sandwiched between a first pair of blocks, said first pair of blocks each having a first face receiving a corresponding first face of said first piezoelectric element whereby said first pair of blocks are coupled to said first piezoelectric element with said first axis being perpendicular to each one of said first faces, said second transducer having a second piezoelectric element sandwiched between a second pair of blocks, said second pair of blocks each having a second face receiving a corresponding second face of said second piezoelectric element whereby said second pair of blocks are coupled to said second piezoelectric element with said second axis being perpendicular to each one of said second faces, each of said first and second pair of blocks being conductive to vibratory frequencies originating from a corresponding one of said first and second piezoelectric elements; and a driver circuit electrically connected to each one of said first and second pairs of blocks of each of said first and second transducers of said transducer assembly, said driver circuit exciting said transducer assembly within a first frequency range and within a second frequency range, said first frequency range including a critical structural resonant frequency for a first type of algae, said second frequency range including a critical structural resonant frequency for a second type of algae.

2. The apparatus of claim 1 further including at least one vibration isolator between said first sonic transducer and said second sonic transducer.

3. The apparatus of claim 1 wherein said transducer assembly is encapsulated in a waterproof compound whereby said transducer assembly is protected from water damage, and said waterproof compound is substantially transparent to sonic waves.

4. The apparatus of claim 1 further including a communications module, said communications module connected to said driver circuit, and said communications module configured to communicate with an external device.

5. The apparatus of claim 4 wherein said communications module receives data from said external device and sends said data to said driver circuit for setting at least one of said plurality of operating characteristics of said first and second transducers.

6. The apparatus of claim 1 wherein said driver circuit controls a plurality of operating characteristics of said transducer assembly, wherein said plurality of operating characteristics are based on a preselected application configuration, wherein said preselected application configuration is a set of operating parameters for a specific set of conditions.

7. The apparatus of claim 1 wherein said driver circuit operatively controls at least one frequency emitted by said transducer assembly within 360 degrees, and said driver circuit operatively controls a power level specific to each one of a plurality of said at least one frequency; wherein said at least one frequency is within a bandwidth determined by a specific microorganism to be targeted by said transducer assembly.

8. The apparatus of claim 1 wherein said driver circuit operatively energizes said transducer assembly with a specified duty cycle.

9. The apparatus of claim 8 in which said specified duty cycle has an on-cycle of 0.4 seconds in which said driver circuit excites at least one of said first and second transducers.

10. The apparatus of claim 1 further including a microorganism sensor responsive to a concentration of at least one type of microorganism in the body of water, said microorganism sensor having an output corresponding to said concentration, said driver circuit controlling said transducer assembly in accordance with said output of said microorganism sensor.

11. The apparatus of claim 1 further including a sensor selected from a group including a moisture sensor, a temperature sensor responsive to a temperature of the body of water, a pressure sensor responsive to a depth of said transducer assembly in said body of water, a g-force sensor responsive to motions of said transducer assembly, and a GPS unit responsive to a location of said apparatus; and said driver circuit responsive to said sensor.

12. The apparatus of claim 1 further including a float having sufficient buoyancy to support said transducer assembly a specified distance below a surface of the body of water.

13. The apparatus of claim 1 wherein said first pair of blocks is secured to said first piezoelectric element with a first electrically conductive adhesive, said second pair of blocks secured to said second piezoelectric element with a second electrically conductive adhesive, whereby said first and second piezoelectric elements are electrically connected to said driver circuit through said first and second pair of blocks.

14. An apparatus for controlling microorganisms in a body of water, said apparatus comprising:

a transducer assembly configured to emit ultrasonic waves along a first axis and along a second axis, said first axis perpendicular to said second axis, said transducer assembly including a first transducer and a second transducer, said first transducer defining said first axis, said second transducer defining said second axis, each one of said first and second transducers having a piezoelectric element and a pair of opposing blocks, each one of said pair of opposing blocks engaging a corresponding opposing surface of said piezoelectric element, each of said pair of opposing blocks being conductive to vibratory frequencies originating from a corresponding one of said first and second piezoelectric elements;

a driver circuit electrically connected to said transducer assembly, said driver circuit exciting said transducer assembly; and a housing containing said transducer assembly, said housing being waterproof, and said housing connected to a support structure that suspends said housing below a surface of the body of water.

15. The apparatus of claim 14 further including a communications module, said communications module connected to said driver circuit; said communications module receiving data from an external device and send said data to said driver circuit for setting at least one operating parameter of said first and second transducers.

16. The apparatus of claim 14 wherein said driver circuit is electrically connected to each one of said first and second pair of blocks, for each one of said first and second transducers each one of said pair of opposing blocks having a pair of inside faces each with a recess that receives said corresponding opposing surface of said piezoelectric element.

17. An apparatus for controlling microorganisms in a body of water, said apparatus comprising:

a first transducer having a first piezoelectric element and a first pair of blocks, each one of said first pair of blocks having a first face with a recess dimensioned to receive a corresponding face of said first piezoelectric element, each said corresponding face of said first piezoelectric element secured in said recess with an electrically conductive adhesive, said first transducer defining a first axis that is perpendicular to said first face of each one of said first pair of blocks, said first pair of blocks conductive to vibratory frequencies originating from said first piezoelectric element, said first axis coaxial with an emitted first sonic wave;

a driver circuit having an exciter electrically connected to said first pair of blocks in said first transducer;

a power unit in communication with said driver circuit, said power unit providing power to said driver circuit;

a float supporting said first transducer below a surface of the body of water with said first axis substantially parallel with the surface of the body of water when said float and said first transducer are deployed in the body of water; and an anchor system that maintains said float at a selected position when said float is deployed in the body of water.

18. The apparatus of claim 17 further including a second transducer having a second piezoelectric element and a second pair of blocks, each one of said second pair of blocks having a first face with a recess dimensioned to receive a corresponding face of said second piezoelectric element, each said corresponding face of said second piezoelectric element secured in said recess with an electrically conductive adhesive, said second transducer defining a second axis that is perpendicular to said first face of each one of said second pair of blocks, said second pair of blocks conductive to vibratory frequencies originating from said piezoelectric element, said second axis coaxial with an emitted second sonic wave, said second axis perpendicular to said first axis, and said exciter electrically connected to said second pair of blocks in said second transducer.

19. The apparatus of claim 17 wherein said driver circuit includes a processor programmed to control said exciter such that said first transducer is energized with a duty cycle having at least one on-cycle of 0.4 seconds.

20. The apparatus of claim 17 wherein said exciter causes said emitted sonic wave to be variable across a plurality of frequencies with each one of said plurality of frequencies emitted sequentially for an on-cycle period.

* * * * *